United States Patent [19]

Omodei-Sale et al.

[11] 4,379,155
[45] Apr. 5, 1983

[54] 3,5-DISUBSTITUTED-1H-1,2,4-TRIAZOLE DERIVATIVES

[75] Inventors: Amedeo Omodei-Sale, Voghera; Pietro Consonni, Milan; Giulio Galliani, Monza, all of Italy; Leonard J. Lerner, Cranbury, N.J.

[73] Assignee: Gruppo Lepetit S.p.A., Milan, Italy

[21] Appl. No.: 284,033

[22] Filed: Jul. 17, 1981

Related U.S. Application Data

[63] Continuation-in-part of Ser. No. 254,816, Apr. 16, 1981, abandoned, which is a continuation-in-part of Ser. No. 47,411, Jun. 11, 1979, abandoned, which is a continuation-in-part of Ser. No. 11,297, Feb. 12, 1979, abandoned, which is a continuation-in-part of Ser. No. 897,313, Apr. 18, 1978, abandoned.

[51] Int. Cl.$^3$ .................... A61K 31/41; C07D 249/08
[52] U.S. Cl. ............................... 424/269; 260/453.7; 549/436; 549/442; 564/149; 564/150
[58] Field of Search ..................... 548/262; 424/269

[56] References Cited

U.S. PATENT DOCUMENTS

| | | | |
|---|---|---|---|
| 3,879,404 | 4/1975 | Baldwin et al. | 548/262 |
| 4,007,276 | 2/1977 | Omodei-Sale | 548/262 |
| 4,119,635 | 10/1978 | Omodei-Sale et al | 548/262 |

FOREIGN PATENT DOCUMENTS

| | | | |
|---|---|---|---|
| 50-4075 | 1/1975 | Japan | 548/262 |
| 1096600 | 12/1967 | United Kingdom | 548/262 |
| 1351430 | 5/1974 | United Kingdom | 548/262 |

OTHER PUBLICATIONS

Potts, J. Chem. Soc., (1954), pp. 3461–3464.
Liljegrin et al., J. Chem. Soc., (1961), pp. 518–522.
Lopyrev et al., Chem. Abstracts, vol. 85, Abstract No. 1239321 (1976).
Raines, Chem. Abstracts, vol. 55, Col. 22615h (1961).

*Primary Examiner*—Alton D. Rollins

[57] ABSTRACT

New 3,5-disubstituted 1H-1,2,4-triazoles of formula I

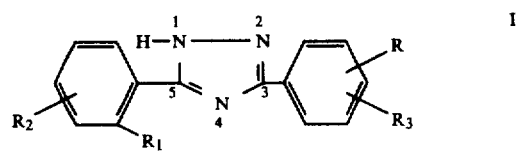

wherein:
R is selected from hydrogen, $(C_{1-4})$alkyl, $(C_{1-4})$alkoxy, allyloxy, propargyloxy, trifluoromethyl, phenyl, fluoro, chloro and dimethylamino;
$R_1$ represents a $(C_{1-4})$alkyl group;
$R_2$ is selected from hydrogen, fluoro, chloro, $(C_{1-4})$alkyl, methoxy and ethoxy;
$R_3$ is selected from hydrogen, fluoro, chloro, $(C_{1-4})$alkyl and $(C_{1-4})$alkoxy;
R and $R_3$ taken together represent a methylenedioxy group; with the proviso that, when R, $R_2$ and $R_3$ simultaneously represent hydrogen, $R_1$ cannot be methyl;
with the further proviso that, when $R_2$ and one of R and $R_3$ simultaneously represent hydrogen, $R_1$ and the other of R and $R_3$ cannot simultaneously represent methyl; and with the still further proviso that compounds of formula I are excluded wherein $R_2$ is hydrogen and one of R and $R_3$ is simultaneously a 2-positioned alkyl group and the other of R and $R_3$ is hydrogen; and salts thereof with pharmaceutically acceptable acids. The compounds possess anti-reproductive utility.

9 Claims, No Drawings

3,5-DISUBSTITUTED-1H-1,2,4-TRIAZOLE DERIVATIVES

CROSS-REFERENCE TO RELATED APPLICATIONS

This application is a continuation-in-part of U.S. patent application Ser. No. 254,816 filed Apr. 16, 1981, now abandoned which in turn is a continuation-in-part of U.S. patent application Ser. No. 047,411 filed June 11, 1979, now abandoned, which in turn is a continuation-in-part of U.S. patent application Ser. No. 011,297, filed Feb. 12, 1979, now abandoned, which in turn is a continuation-in-part of U.S. patent application Ser. No. 897,313, filed Apr. 18, 1978 now abandoned.

The present invention refers to new 3,5-disubstituted-1H-1,2,4-triazoles of the formula

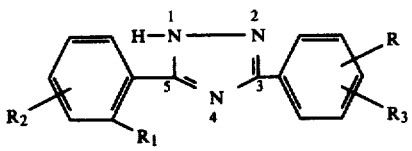

wherein:
R is selected from hydrogen, $(C_{1-4})$alkyl, $(C_{1-4})$alkoxy, allyloxy, propargyloxy, trifluoromethyl, phenyl, fluoro, chloro and dimethylamino;
$R_1$ represents a $(C_{1-4})$alkyl group;
$R_2$ is selected from hydrogen, fluoro, chloro, $(C_{1-4})$alkyl, methoxy and ethoxy;
$R_3$ is selected from hydrogen, fluoro, chloro, $(C_{1-4})$alkyl and $(C_{1-4})$alkoxy;
R and $R_3$ taken together represent a methylenedioxy group; with the proviso that, when R, $R_2$ and $R_3$ simultaneously represent hydrogen, $R_1$ cannot be methyl;
with the further proviso that, when $R_2$ and one of R and $R_3$ simultaneously represent hydrogen, $R_1$ and the other of R and $R_3$ cannot simultaneously represent methyl; and with the still further proviso that compounds of formula I are excluded wherein $R_2$ is hydrogen and one of R and $R_3$ is simultaneously a 2-positioned alkyl group and the other of R and $R_3$ is hydrogen; and salts thereof with pharmaceutically acceptable acids.

The compounds possess anti-reproductive utility.

The expression "$(C_{1-4})$alkyl" as used herein identifies straight or branched alkyl radicals selected from methyl, ethyl, propyl, isopropyl, butyl, isobutyl, sec-butyl and tert.-butyl. The term "$(C_{1-4})$alkoxy" as used herein identifies straight or branched alkoxy radicals selected from methoxy, ethoxy, propoxy, isopropoxy, butoxy, isobutyloxy and tert.-butoxy.

3,5-Disubstituted-1,2,4-triazoles bearing a $(C_{1-4})$alkyl substituent at the 1-positioned triazole nitrogen atom, with CNS-depressant activity are described in U.S. Pat. No. 4,119,635, while 3,5-diphenyl-1,2,4-triazole, as well as its CNS-stimulating and depressing effects, are described in Chemical Abstracts, Vol. 55, column 22615 h (1961).

The use of symmetrical 3,5-bis(substituted or unsubstituted phenyl)-1,2,4-triazoles as starting materials for preparing 3,5-bis(substituted or unsubstituted aminophenyl)-1,2,4-triazoles useful as intermediates for dyestuffs and pigments, starting materials for heat resistant synthetic resins, additives for synthetic resins, and further, organic electro-conductive materials is generically taught by Japanese patent application Ser. No. 56482/73 (Publication No. 4075/75). The use of 3,5-diphenyl-, 3,5-bis(3-methylphenyl)-, and 3,5-bis(4-chlorophenyl)-1,2,4-triazole is described in particular.

The compounds known from the above prior-art references structurally differ from the compounds of the present invention in the presence of an alkyl substituent at the triazole nitrogen atom and/or in the absence of an alkyl substituent at the ortho position of one of the phenyl groups. These differences in structure lead to compounds having no anti-reproductive activity or in any case much lower than that of the compounds of the present invention. The absence of substitution at the triazole nitrogen atom as well as the presence of an alkyl substituent at the ortho position of one of the phenyl groups are in fact structural requirements which are strictly necessary for the compounds to be useful as antifertility agents.

A preferred group of compounds comprises those compounds of formula I wherein R is selected from hydrogen, $(C_{1-4})$alkyl, $(C_{1-4})$alkoxy, allyloxy, fluoro, chloro and dimethylamino, $R_1$ represents $(C_{1-4})$alkyl, $R_2$ is selected from hydrogen, chloro, fluoro, $(C_{1-4})$alkyl, methoxy and ethoxy, $R_3$ may be hydrogen, $(C_{1-4})$alkoxy, fluoro or chloro, R and $R_3$ taken together represent a methylenedioxy group; with the proviso that, when R, $R_2$ and $R_3$ simultaneously represent hydrogen, $R_1$ cannot be methyl; with the further proviso that, when $R_2$ and $R_3$ simultaneously represent hydrogen, R and $R_1$ may not simultaneously be methyl; and salts thereof with pharmaceutically acceptable acids.

Another preferred group of compounds comprises those compounds of formula I wherein R is selected from hydrogen, $(C_{1-4})$alkoxy, allyloxy, fluoro and chloro, $R_1$ represents $(C_{1-4})$alkyl, $R_2$ is selected from hydrogen, chloro, methyl and methoxy, $R_3$ may be hydrogen or $(C_{1-4})$alkoxy, R and $R_3$ taken together represent a methylenedioxy group; with the proviso that, when R, $R_2$ and $R_3$ simultaneously represent hydrogen, $R_1$ cannot be methyl; and salts thereof with pharmaceutically acceptable acids.

A most preferred group of compounds comprises those compounds of formula I wherein R is selected from hydrogen, methoxy, ethoxy, allyloxy, fluoro and chloro, $R_1$ is a $(C_{1-4})$alkyl group, $R_2$ is selected from hydrogen, chloro, methyl and methoxy, $R_3$ is hydrogen or methoxy, R and $R_3$ taken together represent a methylenedioxy group; with the proviso that, when R, $R_2$ and $R_3$ simultaneously represent hydrogen, $R_1$ cannot be methyl; and salts thereof with pharmaceutically acceptable acids.

It will result to any person skilled in the art that, owing to the great mobility of the hydrogen atom of 1,2,4-triazoles (see K. T. Potts, Chem. Rew. 61, 99, 1961 and, again, K. T. Potts, J. Chem. Soc. 3451, 1954), the compounds of the invention may also exist as the corresponding tautomeric forms wherein the hydrogen atom is located on one of the other two nitrogen atoms of the triazole nucleus. Accordingly, said tautomeric forms have to be considered as a part of the invention.

It is known that tautomeric forms rapidly exchange into each other and are, therefore, in a state of dynamic equilibrium. In any case, throughout the specification, the 3,5-disubstituted-1H-1,2,4-triazole derivatives of the present invention will be numbered as in formula I.

The method for preparing the 3,5-disubstituted-1H-1,2,4-triazoles of the invention comprises reacting a compound of formula

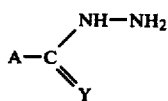

or an acid salt thereof, e.g., the hydrochloride, with a compound of formula

B-CX    III wherein

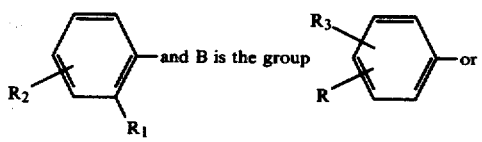

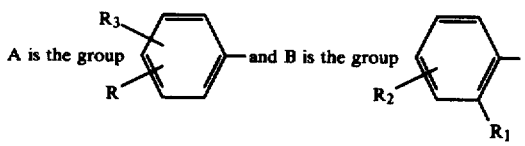

In the above formulas the radicals R, $R_1$, $R_2$ and $R_3$ have the same meanings as before, CX is a functional group selected from carboxy, dithiocarboxy, carbonyl halide, carboxy anhydride, orthoester, imidate, thioimidate, imidoyl halogenide, amidino and cyano; Y is a group NH and, when the group CX contains a nitrogen atom, it represents oxygen or sulfur.

When the group CX represents imidate, thioimidate, imidoyl halogenide or amidino, also the compound of formula III may be employed as the corresponding acid salt.

The process which leads to the 1,2,4-triazoles of the invention is a condensation reaction during which, depending on the nature of the reacting groups Y and CX, water, hydrogen sulfide, hydrogen halide, ammonia, alkanols, mercaptans, carboxylic acids or mixtures thereof are formed as the by-products. These by-products can be eliminated during the course of the reaction or are removed at the end of the condensation by means of usual procedures.

In the actual practice the condensation reaction is carried out by heating under stirring the pair of reactants of formulas II and III, generally in the absence of the solvent, at a temperature of from about 80° to about 200° C. for a time varying from about 15 to about 30 hours. A slight molar excess over the compound of formula II of the compound containing the CX function may be advantageously employed. Preferably, the CX function is an imidate group of formula

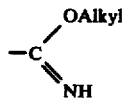

wherein Alkyl may be methyl, ethyl or propyl, so that the low boiling alcohol which forms during the condensation, e.g. methanol, ethanol or propanol, automatically evaporates from the reaction medium. In order to speed up the removal of the alcohol, a moderate vacuum may be conveniently applied. It has also been observed that the presence of an acidic catalyst may favor the condensation reaction and, therefore, a catalytic amount of hydrochloric or hydrobromic acid, or p-toluenesulfonic acid may be conveniently added to the reaction mixture. This addition is not necessary when the reactants are employed as the corresponding acid salts. Finally, if during the heating the reaction mass tends to solidify, it may be advantageous to add to the mass a small amount of an organic solvent such as, for instance, n-butanol, n-pentanol, acetonitrile, tetrahydrofuran and analogs. This solvent is evaporated off in vacuo at the end of the reaction. The final products are then recovered according to known procedures. As an example, the reaction mixture is taken up with a suitable organic solvent, preferably diethylether, and the organic solution is extracted several times with dilute sodium hydroxide. The alkaline extracts are combined together and, if necessary, treated with charcoal in order to remove impurities. After filtering on celite, the filtrate is brought to a pH value of about 6–7 by adding dilute hydrochloric acid. A product separates which may be solid or oily. Depending on its nature, it may be recovered by filtration or extracted with a suitable organic solvent, as an example diethylether or methylenechloride. Said solvent is then evaporated off leaving a solid crystalline residue.

A further purification by column chromatography may be sometimes necessary. Finally, the desired 3,5-disubstituted-1H-1,2,4-triazole derivatives are recrystallized from suitable organic solvents, such as, for instance, hexane, methylene chloride, chloroform, di-isopropylether, benzene, cyclohexane or mixtures thereof.

The 3,5-disubstituted-1H-1,2,4-triazoles of the present invention possess anti-reproductive utility. More particularly, they show a very interesting post-coital-post-implantation antifertility activity when administered by different pharmacological routes, to laboratory animals, e.g. rats, hamsters, dogs, monkeys and baboons.

Moreover, the antifertility activity of these new compounds is not associated with other biological effects which are usual with hormonal substances.

Fertility regulation can usually be achieved in a number of ways through the administration of hormonal substances. These can involve ovulation inhibition, ova transport, fertilization, implantation of the zygote, resorption of the fetus or abortion. Only with ovulation inhibition has there developed a successful method that is clinically useful.

The compounds of this invention allow an entirely new approach to this problem in which a non-hormonal compound can be administed parenterally, orally or by intravaginal route once or more times as needed after a "missed period" or to induce termination of a more advanced pregnancy. Representative experiments for assessing antifertility activity were carried out with femal Syrian golden hamsters weighing 100 to 130 g. The animals were mated and the presence of sperm in the vagina was taken as evidence of mating. The day sperm was detected was considered day one of pregnancy, since in our laboratories and those of other investigators 90 to 100% of animals that mate as evidenced by vaginal sperm are pregnant. Pregnancy was later confirmed at the time of autopsy by presence of fetuses or implantation sites in the uterus. Even if an animal aborts the fetus, implantation scars still remain as evidence that the animal has been pregnant.

The compounds of the invention, which possess a high solubility in the commonly employed pharmaceutical vehicles, were dissolved in sesame oil and administered subcutaneously in doses of 10 mg/kg daily for 5 days beginning on day 4 of pregnancy (days 4-8). The animals were autopsied on day 14 of pregnancy and the uteri were examined for evidence of pregnancy (implantation sites, fetal resorptions or live fetuses), hemorrage, and evidence of abnormalities of the uterus, placenta or fetuses. A compound was considered to be active if there was a reduction of live fetuses in at least 60% of the treated animals and the presence of implantation sites proved the animal to have been pregnant. In representative experiments the compounds of Examples 1, 4, 5-7, 9-16, 18, 22, 25, 26, 29, 30, 32 and 34-37 proved to be active according to the above mentioned criteria, whereas the 3,5-diphenyl-1H-1,2,4-triazole, described by Raines, in J. Pharm. Sci., 50, 597, 1961 (see also Chem. Abs. 55, 22615h, 1961) was much less active.

The compounds were then studied for dose-activity relationships and the corresponding $ED_{50}$ values i.e., 100% activity (absence of live fetuses) in 50% of the animals, were also determined. The following table reports the $ED_{50}$ values of some representative compounds of the invention in comparison with the above mentioned 3,5-diphenyl-1H-1,2,4-triazole.

TABLE I

| Compound -1H—1,2,4-triazole | $ED_{50}$ mg/kg s.c. hamsters |
|---|---|
| 3-(m-Methoxyphenyl)-5-(o-tolyl)- | 0.08 |
| 3-(o-Methoxyphenyl)-5-(o-tolyl)- | 0.5 |
| 3-(m-Ethoxyphenyl)-5-(o-tolyl)- | 0.07 |
| 3-(m-Allyloxyphenyl)-5-(o-tolyl)- | 0.25 |
| 5-(o-Ethylphenyl)-3-(m-methoxyphenyl)- | 0.04 |
| 3-(m-Allyloxyphenyl)-5-(o-ethylphenyl)- | 0.1 |
| 3-(m-Ethoxyphenyl)-5-(o-ethylphenyl)- | 0.04 |
| 5-(o-Ethylphenyl)-3-(p-methoxyphenyl)- | 0.15 |
| 5-(o-Ethylphenyl)-3-(m-fluorophenyl)- | 0.4 |
| 5-(o-Ethylphenyl)-3-(3,4-methylenedioxyphenyl)- | 0.03 |
| 5-(o-Ethylphenyl)-3-(3,4-dimethoxyphenyl) | 0.05 |
| 5-(2,4-Dimethylphenyl)-3-phenyl- | 0.2 |
| 5-(2,4-Dimethylphenyl)-3-(m-methoxyphenyl)- | 0.04 |
| 5-(4-Chloro-2-methylphenyl)-3-phenyl- | 0.14 |
| 5-(4-Chloro-2-methylphenyl)-3-(m-methoxyphenyl)- | 0.04 |
| 5-(5-Chloro-2-methylphenyl)-3-(m-methoxyphenyl)- | 0.35 |
| 5-(4-Methoxy-2-methylphenyl)-3-(m-methoxyphenyl)- | 0.2 |
| 3,5-Diphenyl- | 6 |

The same criteria and experimental conditions as above were also applied when the anti-reproductive activity of the compounds of the invention was investigated in other animal species such as, for instance, rats, dogs, monkeys and baboons. In representative experiments, female Sprague-Dawley rats weighing from 200 to 300 g. were treated subcutaneously with a dosage of 20 mg/kg of the compound to be tested, dissolved in sesame oil, for five consecutive days starting from day 6 of pregnancy. The rats were killed and autopsied on day 16 and the uteri were examined as seen above for hamsters. Also in this experiment the compounds of Examples 1, 4, 5-7, 9-16, 18, 22, 25, 26, 29, 30, 32 and 34-37 caused a reduction of live fetuses in at least 60% of the treated rats. The $ED_{50}$ values of the compounds of Examples 1 and 12 were determined and are reported in the following Table:

TABLE II

| Compound —1H—1,2,4-triazole | $ED_{50}$ mg/kg s.c. rats |
|---|---|
| 3-(m-Methoxyphenyl)-5-(o-tolyl)- | 1 |
| 5-(o-Ethylphenyl)-3-(m-methoxyphenyl)- | 0.7 |

Favorable results were also obtained by administering the compounds of the invention by oral route. The experiments for assessing this property were carried out on hamsters following the same procedure as above, with the obvious exception that the compounds were administered orally instead of subcutaneously.

The reduction of about 60% of live fetuses was observed at an oral dosage of 10 mg/kg with compounds of Examples 1, 4, 5-7, 19-16, 18, 22, 25, 26, 29, 30, 32 and 34-37. The oral $ED_{50}$ values of some representative compounds of the invention are reported in the following table:

TABLE III

| Compound —1H—1,2,4-triazole | $ED_{50}$ mg/kg p.o. hamsters |
|---|---|
| 3-(m-Methoxyphenyl)-5-(o-tolyl)- | 5 |
| 5-(o-Ethylphenyl)-3-(m-methoxyphenyl)- | 5 |
| 3-(m-Ethoxyphenyl)-5-(o-ethylphenyl)- | 3 |
| 5-(o-Ethylphenyl)-3-(p-methoxyphenyl)- | 5 |
| 5-(o-Ethylphenyl)-3-(3,4-methylenedioxyphenyl)- | 3 |
| 5-(4-Chloro-2-methylphenyl)-3-(m-methoxyphenyl)- | 5 |

Finally, the compounds of the invention display a very low toxicity. In their $LD_{50}$-values, determined according to Lichtfield and Wilcoxon, Journ. Pharm. Expt. Ther., 96, 99, 1949, are never lower than 600 mg/kg, when administered to mice by intraperitoneal route.

The facts that the compounds of the invention possess an outstanding antireproductive activity even when administered by oral route and are very soluble in the common pharmaceutical carriers represent undoubtedly further important properties. As an example, the high solubility causes the compounds to be readily absorbable and incorporable into suitable and more tolerable injectable dosage forms which possess less drawbacks than corresponding forms wherein the active ingredient is suspended in the carrier. On the other hand, also the activity by oral route allows the compounds to be embodied into more acceptable pharmaceutical preparations.

It derives, therefore, that the compounds of the invention may be administered by various routes: orally, subcutaneously, intramuscularly or intravaginally. For oral administration the substances are compounded in such forms as tablets, dispersible powders, capsules, granules, syrups, elixirs and solutions.

The compositions for oral use may contain one or more conventional adjuvants, such as, for instance, sweetening agents, flavoring agents, coloring agents, coating and preservative agents, in order to provide an elegant and palatable preparation.

Tablets may contain the active ingredient admixed with conventional pharmaceutical acceptable excipients, e.g. inert dilutes such as calcium carbonate, sodium carbonate, lactose and talc, granulating and disintegrating agents, such as, for instance, starch, alginic acid and sodium carboxymethylcellulose, binding agents, e.g. starch, gelatin, gum-arabic and polyvinylpyrrolidone and lubricating agents, e.g. magnesium stearate, stearic acid and talc.

Syrups, elixirs and solutions are formulated as known in the art. Together with the active compound they may contain suspending agents, such as, for instance, methylcellulose, hydroxyethylcellulose, tragacanth and sodium alginate, wetting agents, e.g. lecithin, polyoxyethylene stearates and polyoxyethylene sorbitan monooleate, and the common preservative, sweetening and buffering agents.

A capsule or a tablet may contain the active ingredient alone or admixed with an inert solid diluent, such as, for instance, calcium carbonate, calcium phosphate and kaolin.

Besides the oral route, other useful ways for administering the compounds of the invention may be suitably employed, such as, for instance, the subcutaneous or the intramuscular administration.

The active ingredient is thus embodied into injectable dosage forms. Such compositions are formulated according to the art and may contain appropriate dispersing or wetting agents and suspending or buffering agents identical or similar to those mentioned above.

Sesame oil, benzyl alcohol, benzyl benzoate, peanut oil and their mixtures may also be suitably employed as vehicles.

A vaginal insert may also contains the active ingredient in admixture with the common carriers e.g. gelatin, adipic acid, sodium bicarbonate, lactose and analogs.

The compounds of the invention may also be administered in the form of their non toxic pharmaceutically acceptable acid addition salts. Such salts possess the same degree of activity as the free bases, from which they are readily prepared by reacting the base with an appropriate acid and accordingly, are included within the scope of the invention. Representative of such salts are the mineral acid salts, such as, for instance, the hydrochloride, hydrobromide, sulfate and the like and the organic acid salts such as the succinate, benzoate, acetate, p-toleuenesulfonate, benzene sulfonate, maleate, tartrate, methanesulfonate, cyclohexylsulfonate and the like.

The dosage of active ingredient employed for inhibiting reproduction may vary within wide limits, depending on the nature of the compound.

Generally, good results are obtained when the compounds of the above formula I are administered at a daily dosage from about 0.8 to about 50 mg/kg of animal body weight.

The dosages forms useful for this purpose generally contains from about 10 to about 600 mg of the active ingredient in admixture with a solid or liquid pharmaceutically acceptable carrier or diluent.

The following examples illustrate the process of the invention and describe in detail some compounds of the general formula I without limiting the scope of the invention.

EXAMPLE 1

3-(m-Methoxyphenyl)-5-(o-tolyl)-1H-1,2,4-triazole

A mixture of 3.0 g. (0.02 mole) of the hydrazide of o-toluic acid and 4.83 g. (0.027 mole) of m-methoxybenzimidic acid ethyl ester was heated on an oil bath under stirring for about 20 hours, keeping the temperature of the bath at about 125° C. After cooling, the reaction mass was taken up with 100 ml. of diethyl ether and the obtained ether solution was first extracted with 50 ml of 5% aqueous sodium hydroxide and then twice with 30 ml of water. The water and alkaline extracts were combined together, treated with charcoal to remove any impurity and filtered on celite. The filtrate was brought to pH 7 by adding under stirring 10% aqueous hydrochloric acid whereby an oily substance separated which was extracted with diethyl ether. After drying over sodium sulfate, the ether was evaporated off in vacuo and the obtained residue was recrystallized from diisopropyl ether/hexane. Yield 3.15 g. M.p. 100°-2° C.

EXAMPLES 2-5

Following substantially the same procedures described in Example 1, the following compounds were prepared.

EXAMPLE 2

3-(p-Dimethylaminophenyl)-5-(o-tolyl)-1H-1,2,4-triazole from 2.55 g.

(0.017 mole) of the hydrazide of o-toluic acid and 4.26 g. (0.021 mole) of p-dimethylaminobenzimidic acid ethyl ester. Yield 3.04 g. M.p. 173°-75° C. (from diisopropyl ether).

EXAMPLE 3

3-(o-Chlorophenyl)-5-(o-tolyl)-1H-1,2,4-triazole, from 3.75 g.

(0.025 mole) of the hydrazide of o-toluic acid and 5.5 g. (0.03 mole) of o-chlorobenzimidic acid ethyl ester. Yield 4.26 g. M.p. 109°-11° C. (from hexane/methylene chloride).

EXAMPLE 4

3-(o-Methoxyphenyl)-5-(o-tolyl)-1H-1,2,4-triazole, from 6.75 g.

(0.045 mole) of the hydrazide of o-toluic acid and 9.85 g. (0.05 mole) of o-methoxybenzimidic acid ethyl ester. Yield 4.81 g. M.p. 160°-61° C. (from hexane/diisopropyl ether)

EXAMPLE 5

3-(m-Chlorophenyl)-5-(o-tolyl)-1H-1,2,4-triazole, from 2.55 g.

(0.017 mole) of the hydrazide of o-toluic acid and 4.1 g. (0.0221 mole) of m-chlorobenzimidic acid ethyl ester. Yield 2.34 g. M.p. 147°-48° C. (from cyclohexane/benzene)

EXAMPLE 6

3-(m-Trifluoromethylphenyl)-5-(o-tolyl)-1H-1,2,4-triazole

A mixture of 2.55 g (0.017 mole) of the hydrazide of o-toluic acid and 4.8 g (0.0221 mole) of m-trifluoromethylbenzimidic acid ethyl ester was heated on an oil bath for 6 hours under stirring, keeping the temperature of the bath at about 125° C. A solid mass formed which was added with 15 ml of n-butanol, and the resulting mixture was heated for about 19 hours keeping the temperature of the oil bath at about 125° C.

During this period, the solid mass completely dissolved in the butanol which, at the end of the reaction, was evaporated off in vacuo, bringing the temperature of the oil bath to about 150° C. After cooling, the reaction mass was taken up with diethyl ether, the ether solution was extracted with 120 ml of 5% aqueous sodium hydroxyde and then twice with 50 ml of water and the water and alkaline extracts were combined together. After treatment with charcoal to remove any impurity and subsequent filtration on celite, the filtrate was brought to pH 7 by adding, under stirring, 10% aqueous hydrochloric acid. A precipitate formed, which was collected and recrystallized from cyclohexane/benzene. Yield 2.55 g. M.p. 158°-59° C.

EXAMPLES 7-17

These compounds were prepared substantially as described in Example 6.

EXAMPLE 7

3-(p-Fluorophenyl)-5-(o-tolyl)-1H-1,2,4-triazole from 2.03 g.

(0.0135 mole) of the hydrazide of o-toluic acid and 2.95 g. (0.0175 mole) of p-fluorobenzimidic acid ethyl ester. Yield 1.18 g. M.p. 119°-21° C. (from hexane/diisopropyl ether).

EXAMPLE 8

3-(p-Chlorophenyl)-5-(o-tolyl)-1H-1,2,4-triazole from 2.03 g.

(0.0135 mole) of the hydrazide of o-toluic acid and 3.25 g (0.0175 mole) of p-chlorobenzimidic acid ethyl ester. Yield 1.13 g. M.p. 150°-151° C. (from diisopropyl ether). The compound contains half molecule of crystallization water.

EXAMPLE 9

3-(m-Ethoxyphenyl)-5-(o-tolyl)-1H-1,2,4-triazole from 1.5 g.

(0.01 mole) of the hydrazide of o-toluic acid and 2.12 g (0.011 mole) of m-ethoxybenzimidic acid ethyl ester. Yield 1.41 g. M.p. 84°-86° C. (from diisopropyl ether).

EXAMPLE 10

3-(m-Allyloxyphenyl)-5-(o-tolyl)-1H-1,2,4-triazole from 1.5 g.

(0.01 mole) of the hydrazide of o-toluic acid and 2.26 g (0.011 mole) of m-allyloxy-benzimidic acid ethyl ester. Yield 1.89 g. M.p. 72°-75° C. (from diisopropyl ether)

EXAMPLE 11

3-(1,1'-Biphenyl-4-yl)-5-(o-tolyl)-1H-1,2,4-triazole from 0.99 g.

(0.0066 mole) of the hydrazide of o-toluic acid and 1.68 g. (0.0075 mole) of p-phenyl-benzimidic acid ethyl ester. Yield 1.47 g. M.p. 165°-67° C. (from cyclohexane/benzene).

EXAMPLE 12

5-(o-Ethylphenyl)-3-(m-methoxyphenyl)-1H-1,2,4-triazole from 4.87 g.

(0.03 mole) of the hydrazide of o-ethylbenzoic acid and 5.35 g (0.03 mole) of m-methoxy-benzimidic acid ethyl ester. Yield 5.36 g. M.p. 72°-75° C. (from diisopropyl ether/hexane). The hydrochloride melts at 175°-177° C. (from ethanol/ethyl ether). The methane sulfonate melts at 104° C.

EXAMPLE 13

3-(m-Allyloxyphenyl)-5-(o-ethylphenyl)-1H-1,2,4-triazole from 1.64 g.

(0.01 mole) of the hydrazide of o-ethylbenzoic acid and 2.26 g (0.011 mole) of m-allyloxy-benzimidic acid ethyl ester. Yield 2.73 g. M.p. (as the hydrochloride) 130°-32° C. (from ethanol).

EXAMPLE 14

3-(p-Chlorophenyl)-5-(o-ethylphenyl)-1H-1,2,4-triazole from 1.64 g.

(0.01 mole) of the hydrazide of o-ethylbenzoic acid and 2.01 g. (0.011 mole) of p-chlorobenzimidic acid ethyl ester. Yield 1.32 g. M.p. 118°-120° C. (from diisopropyl ether/hexane).

EXAMPLE 15

5-(o-Isopropylphenyl)-3-phenyl-1H-1,2,4-triazole from 1.25 g.

(0.007 mole) of the hydrazide of 2-isopropylbenzoic acid and 1.15 g (0.0077 mole) of benzimidic acid ethyl ester. Yield 1.38 g. M.p. 165°-67° C. (from diisopropyl ether/light petroleum)

EXAMPLE 16

5-(o-Isopropylphenyl)-3-(m-methoxyphenyl)-1H-1,2,4-triazole from 1.78

(0.01 mole) of the hydrazide of 2-isopropylbenzoic acid and 1.97 g (0.011 mole) of m-methoxy-benzimidic acid ethyl ester. Yield 2.27 g M.p. 125°-26° C. (from diisopropyl ether/light petroleum).

EXAMPLE 17

5-(o-Ethylphenyl)-3-phenyl-1H-1,2,4-triazole from 1.64 g.

(0.01 mole) of the hydrazide of o-ethylbenzoic acid and 1.49 g. (0.01 mole) of benzimidic acid ethyl ester. Yield 1.77 g. M.p. 124°-26° C. (from diisopropyl ether/hexane).

The starting benzimidic acid ethyl ester derivatives were prepared according to literature methods (Pinner, "Die Imidoäther and Ihre Derivative"; R. Oppenheim, Berlin, 1892: L. Weintraub et al. J. Org. Chem., Vol. 33, No. 4, page 1679, 1968).

The starting hydrazides of o-toluic, o-ethylbenzoic and o-isopropylbenzoic acid were prepared according to Stolle and Stevens, J. Pr /2/, 69, 368 (see also Beilstein, Vol. 9, page 467, J. Springer Verlag, Berlin, 1926).

EXAMPLES 18-37

Other compounds which were prepared according to the procedures described in the above Examples are:

| Ex. | -1H—1,2,4-triazole | M.p. °C. |
|---|---|---|
| 18 | 5-(o-Ethylphenyl)-3-(m-fluorophenyl)- | 112-14 |
| 19 | 5-(o-Ethylphenyl)-3-(2,3-dimethylphenyl)- | 154-55 |
| 20 | 5-(o-Ethylphenyl)-3-(2,3-dimethoxyphenyl)- | 139-41 |
| 21 | 5-(o-Ethylphenyl)-3-(3,5-dimethoxyphenyl)- | 133-35 |
| 22 | 5-(o-Ethylphenyl)-3-(3,4-methylenedioxyphenyl)- | 108-10 |
| 23 | 5-(o-Butylphenyl)-3-phenyl- | 121-22 |
| 24 | 5-(o-Butylphenyl)-3-(m-methoxyphenyl) | 101-02 |
| 25 | 5-(2,4-Dimethylphenyl)-3-phenyl- | 139-41 |
| 26 | 5-(2,4-Dimethylphenyl)-3-(m-methoxyphenyl)- | 106-08 |
| 27 | 5-(2,5-Dimethylphenyl)-3-phenyl- | 147-49 |
| 28 | 5-(2,5-Dimethylphenyl)-3-(m-methoxyphenyl)- | 127-30 |
| 29 | 5-(4-Chloro-2-methylphenyl)-3-phenyl- | 135-36 |
| 30 | 5-(4-Chloro-2-methylphenyl)-3-(m-methoxyphenyl)- | 137-39 |
| 31 | 5-(5-Chloro-2-methylphenyl)-3-phenyl- | 170-72 |
| 32 | 5-(5-Chloro-2-methylphenyl)-3-(m-methoxyphenyl)- | 169-71 |
| 33 | 5-(4-Methoxy-2-methylphenyl)-3-phenyl- | 152-53 |
| 34 | 5-(4-Methoxy-2-methylphenyl)-3-(m-methoxyphen- | 121-22 |

| Ex. | -1H—1,2,4-triazole | M.p. °C. |
|---|---|---|
| | yl)- | |
| 35 | 3-(m-Ethoxyphenyl)-5-(o-ethylphenyl)- | 84–86 |
| 36 | 5-(o-Ethylphenyl)-3-(p-methoxyphenyl)- | 128–29 |
| 37 | 5-(o-Ethylphenyl)-3-(3,4-dimethoxyphenyl)- | 57–60 |

EXAMPLE 38

A vial for injectable use is prepared from:

| | |
|---|---|
| 3-(m-Methoxyphenyl)-5-(o-tolyl)-1H—1,2,4-triazole | 30 mg. |
| Benzyl benzoate | 250 mg. |
| Sesame oil q.s. to | 2 ml. |

EXAMPLE 39

A vial for injectable use is prepared from

| | |
|---|---|
| 3-(m-Ethoxyphenyl)-5-(o-tolyl)-1H—1,2,4-triazole | 30 mg. |
| Benzyl alcohol | 100 mg. |
| Peanut oil q.s. to | 2 ml. |

EXAMPLE 40

A vial for injectable use is prepared from

| | |
|---|---|
| 5-(o-Ethylphenyl)-3-(m-methoxyphenyl)-1H—1,2,4-triazole | 20 mg. |
| Benzyl alcohol | 80 mg. |
| Castor oil q.s. to | 2 ml. |

EXAMPLE 41

A sugar coated tablet is prepared from

| | |
|---|---|
| 3-(m-Methoxyphenyl)-5-(o-tolyl)-1H,1,2,4-triazole | 100 mg. |
| Sodium carboxymethylcellulose | 5 mg. |
| Magnesium stearate | 5 mg. |
| Gelatin | 10 mg. |
| Starch | 10 mg. |
| Saccharose | 25 mg. | gum arabic, lactose, titan dioxide, aluminum lac according to conventional procedures.

EXAMPLE 42

A capsule is prepared from

| | |
|---|---|
| 5-(o-Ethylphenyl)-3-(m-methoxyphenyl)-1H—1,2,4-triazole | 60 mg. |
| Talc | 5 mg. |
| Lactose | 5 mg. |
| Sodium carboxymethylcellulose | 5 mg. |
| Starch q.s. to | 150 mg. |

EXAMPLE 43

A tablet is prepared from

| | |
|---|---|
| 3-(m-Methoxyphenyl)-5-(o-tolyl)-1H—1,2,4-triazole | 100 mg. |
| Levilite | 100 mg. |
| Starch | 80 mg. |
| Magnesium stearate | 10 mg. |

We claim:

1. A 3,5-disubstituted-1H-1,2,4-triazole of the formula

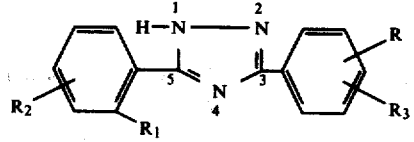

wherein:
R is selected from hydrogen, $(C_{1-4})$alkyl, $(C_{1-4})$alkoxy, allyloxy, propargyloxy, trifluoromethyl, phenyl, fluoro, chloro and dimethylamino;
$R_1$ represents a $(C_{1-4})$alkyl group;
$R_2$ is selected from hydrogen, fluoro, chloro, $(C_{1-4})$alkyl, methoxy and ethoxy;
$R_3$ is selected from hydrogen, fluoro, chloro, $(C_{1-4})$alkyl and $(C_{1-4})$alkoxy;
R and $R_3$ taken together represent a methylenedioxy group, with the proviso that, when R, $R_2$ and $R_3$ simultaneously represent hydrogen, $R_1$ cannot be methyl;
with the further proviso that, when $R_2$ and one of R and $R_3$ simultaneously represent hydrogen, $R_1$ and the other of R and $R_3$ cannot simultaneously represent methyl; and with the still further proviso that compounds of formula I are excluded wherein $R_2$ is hydrogen and one of R and $R_3$ is simultaneously a 2-positioned alkyl group and the other of R and $R_3$ is hydrogen;
or a salt thereof with a pharmaceutically acceptable acid.

2. A compound as defined in claim 1 wherein:
R is selected from hydrogen, $(C_{1-4})$alkyl, $(C_{1-4})$alkoxy, allyloxy, fluoro, chloro and dimethylamino, $R_1$ represents $(C_{1-4})$alkyl, $R_2$ is selected from hydrogen, chloro, fluoro, $(C_{1-4})$alkyl, methoxy and ethoxy, $R_3$ may be hydrogen, $(C_{1-4})$alkoxy, fluoro or chloro, R and $R_3$ taken together represent a methylenedioxy group; with the proviso that, when R, $R_2$ and $R_3$ simultaneously represent hydrogen, $R_1$ cannot be methyl; with the further proviso that, when $R_2$ and $R_3$ simultaneously represent hydrogen, R and $R_1$ may not simultaneously be methyl; and a salt thereof with a pharmaceutically acceptable acid.

3. A compound as defined in claim 1 wherein:
R is selected from hydrogen, $(C_{1-4})$alkoxy, allyloxy, fluoro and chloro, $R_1$ represents $(C_{1-4})$alkyl, $R_2$ is selected from hydrogen, chloro, methyl and methoxy, $R_3$ may be hydrogen or $(C_{1-4})$alkoxy, R and $R_3$ taken together represent a methylenedioxy group; with the proviso that, when R, $R_2$ and $R_3$ simultaneously represent hydrogen $R_1$ cannot be methyl; and a salt thereof with a pharmaceutically acceptable acid.

4. A compound as defined in claim 1 wherein:
R is selected from hydrogen, methoxy, ethoxy, allyloxy, fluoro and chloro, $R_1$ is a $(C_{1-4})$alkyl group, $R_2$ is selected from hydrogen, chloro, methyl and methoxy, $R_3$ is hydrogen or methoxy, R and $R_3$ taken together represent a methylenedioxy group;

with the proviso that, when R, $R_2$ and $R_3$ simultaneously represent hydrogen, $R_1$ cannot be methyl; and a salt thereof with a pharmaceutically acceptable acid.

5. A compound as defined in claim 1 which is 3-(m-methoxyphenyl)-5-(o-tolyl)-1H-1,2,4-triazole.

6. A compound as defined in claim 1 which is 3-(m-ethoxyphenyl)-5-(o-tolyl)-1H-1,2,4-triazole.

7. A compound as defined in claim 1 which is 5-(o-ethylphenyl)-3-(m-methoxyphenyl)-1H-1,2,4-triazole.

8. A pharmaceutical composition for preventing littering in impregnated female animals comprising a pharmaceutical carrier and, as the active ingredient an effective amount of a compound of the formula

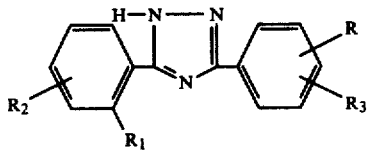

I wherein R, $R_1$, $R_2$ and $R_3$ are defined as in claim 1, or a salt thereof with a pharmaceutically acceptable acid.

9. A pharmaceutical composition as defined in claim 8, wherein the amount of active ingredient varies from about 10 to about 600 mg.

* * * * *